(12) United States Patent
Hartoumbekis

(10) Patent No.: US 8,967,447 B2
(45) Date of Patent: Mar. 3, 2015

(54) SURGICAL INSTRUMENT INCLUDING FIRING INDICATOR

(75) Inventor: Elias Hartoumbekis, New Haven, CT (US)

(73) Assignee: Covidien LP, Mansfield, MA (US)

( * ) Notice: Subject to any disclaimer, the term of this patent is extended or adjusted under 35 U.S.C. 154(b) by 525 days.

(21) Appl. No.: 13/325,364

(22) Filed: Dec. 14, 2011

(65) Prior Publication Data

US 2013/0153632 A1 Jun. 20, 2013

(51) Int. Cl.
*A61B 17/068* (2006.01)

(52) U.S. Cl.
USPC ........................................ 227/176.1

(58) Field of Classification Search
CPC .... A61B 17/00; A61B 17/064; A61B 17/068; A61B 17/07207; A61B 2019/4836; A61B 5/150893
USPC ........................................ 227/176.1
See application file for complete search history.

(56) References Cited

U.S. PATENT DOCUMENTS

| | | | |
|---|---|---|---|
| 5,464,144 A | 11/1995 | Guy et al. | |
| 5,497,934 A | 3/1996 | Brady et al. | |
| 5,503,320 A | 4/1996 | Webster et al. | |
| 5,518,163 A | 5/1996 | Hooven | |
| 5,685,474 A * | 11/1997 | Seeber | 227/179.1 |
| 6,879,880 B2 | 4/2005 | Nowlin et al. | |
| 7,464,847 B2 | 12/2008 | Viola et al. | |
| 2006/0212069 A1 | 9/2006 | Shelton, IV | |
| 2007/0078484 A1 | 4/2007 | Talarico et al. | |
| 2007/0179408 A1 | 8/2007 | Soltz | |
| 2008/0296346 A1 | 12/2008 | Shelton, IV et al. | |
| 2009/0076534 A1 | 3/2009 | Shelton, IV et al. | |
| 2009/0314820 A1 | 12/2009 | Green et al. | |
| 2010/0057105 A1 | 3/2010 | Sorrentino et al. | |
| 2011/0295295 A1 | 12/2011 | Shelton, IV et al. | |

FOREIGN PATENT DOCUMENTS

EP 2 090 255 8/2009

OTHER PUBLICATIONS

European Search Report from European Application No. EP 12 19 6897 mailed Mar. 14, 2013.

* cited by examiner

*Primary Examiner* — Thanh Truong
*Assistant Examiner* — Praachi M Pathak

(57) ABSTRACT

A surgical instrument including a loading unit and an indicator that provides an indication whether the loading unit has been used. The indicator provides an indication by transitioning from a first position to a second position that is viewable by a user to prevent inadvertent reloading of the loading unit after use.

10 Claims, 4 Drawing Sheets

SURGICAL INSTRUMENT INCLUDING FIRING INDICATOR

TECHNICAL FIELD

The present disclosure generally relates to a surgical instrument including a disposable loading unit. More particularly, this disclosure relates to a surgical stapling device providing an indication that the surgical stapling device has been fired.

BACKGROUND

Surgical devices designed to grasp or clamp tissue between a pair of opposing jaws and then joining the tissue with surgical fasteners are well known in the art. In some instruments, a knife is provided to cut the tissue which has been joined by the fasteners. The fasteners are typically in the form of surgical staples, but two part fasteners formed of a material suitable for surgical use can also be used.

Such instruments may include two elongated members adapted to capture or clamp tissue therebetween. Typically, one of the members carries a staple cartridge that houses a plurality of staples arranged in at least two lateral rows while the other member has an anvil defining a surface for forming the staple legs as the staples are driven from the staple cartridge. In some instruments, the closure of the two elongated members, or tool assembly, is effected by the actuation of a movable handle that moves a drive beam having a closure apparatus thereon into a contact surface of a tool assembly thereby actuating the tool assembly. A knife can travel between rows of staples to longitudinally cut and/or open the stapled tissue between the rows of staples.

In laparoscopic and/or endoscopic surgical procedures, the surgical procedure is performed through a small incision or through a narrow cannula inserted through a small entrance wound in a patient. In conventional or open procedures, surgeons directly access an operative site. Because of reduced patient trauma, shortened patient recovery periods and reduced cost, endoscopic procedures are preferred over open surgical procedures.

Articulatable endoscopic stapling instruments including disposable loading units ("DLUs") or singlye use loading units ("SULUs") are known in the art. These instruments have provided significant clinical benefits to the field of endoscopic surgery. Nonethereless, there is a continuing need for surgical devices in this area.

SUMMARY

The present disclosure relates to a surgical instrument including a cartridge assembly. The surgical instrument is usable during many surgical procedures including minimally invasive surgical procedures. The cartridge assembly includes a plurality of fasteners that are ejectable from the cartridge. An indicator assembly provides an indication as to whether the cartridge has been used or not. In an embodiment, the indicator assembly includes an indicator pin that is transitionable from a first position to a second position after ejection of the fasteners, thereby providing visual indication that the fasteners have been ejected from the cartridge. The indicator pin may be inhibited from transitioning from the second position to the first position to inihibit inadvertent reloading of a spent cartridge.

When the indicator pin is in the first position, the indicator pin is substantially flush with a surface of the cartridge. In the second position, the indicator pin extends past the surface of the cartridge, i.e., the indicator pin is not substantially flush with the surface of the cartridge. An actuation sled may distally translate through the cartridge, thereby causing ejection of the fasteners contained therein. The indicator pin may be positioned within a longitudinally extending aperture defined within the distal end of the cartridge. As the actuation sled is translated distally, the actuation sled will abut the indicator pin and force the indicator pin to translate distally, thereby transitioning the indicator pin to the second position to indicate that the fasteners have been ejected from the cartridge.

The indicator assembly may include an assembly that inhibits premature transitioning of the indicator to the second position. For example, the indicator assembly may include a ring that is positioned within an aperture formed in the distal end of the cartridge. The ring is disposed around the indicator pin and releasably locks the indicator pin within the aperture. One or more frangible fingers may couple the indicator pin to the ring by breaking only in response to force resulting from the actuation sled of the drive assembly distally translating through the cartridge and pressing against a proximal end of the indicator pin, thereby allowing the indicator pin to translate distally.

Once the indicator pin has been translated distally, the indicator pin remains extended. The longitudinally extending aperture in which the indicator pin is positioned may narrow toward the distal end of the cartridge, thereby creating an interference fit between the indicator pin and the longitudinally extending aperture, thereby frictionally securing the indicator pin in the extended position.

A method of performing a surgical procedure includes providing a surgical instrument including a cartridge, such as that described above. The indicator pin is operatively coupled to the tool assembly such that after actuation of the surgical instrument, a user is readily notified that the cartridge has been spent. During use, tissue that is to be fastened is placed between the anvil and the cartridge, and the surgical instrument is actuated. Once the surgical instrument is actuated, the indicator assembly transitions to a second position to provide visual indication that the surgical instrument has been fired. Because the indicator pin extends a distance from one of the cartridge or the anvil, the indicator pin is viewable from multiple orientations, thereby readily providing notification to the user that the cartridge has been spent.

The various aspects of the present disclosure will be more readily understood from the following detailed description when read in conjunction with the appended figures.

DESCRIPTION OF THE DRAWINGS

Various embodiments of the presently disclosed surgical instrument are disclosed herein with reference to the drawings, wherein.

DETAILED DESCRIPTION OF EMBODIMENTS

Figure 1:
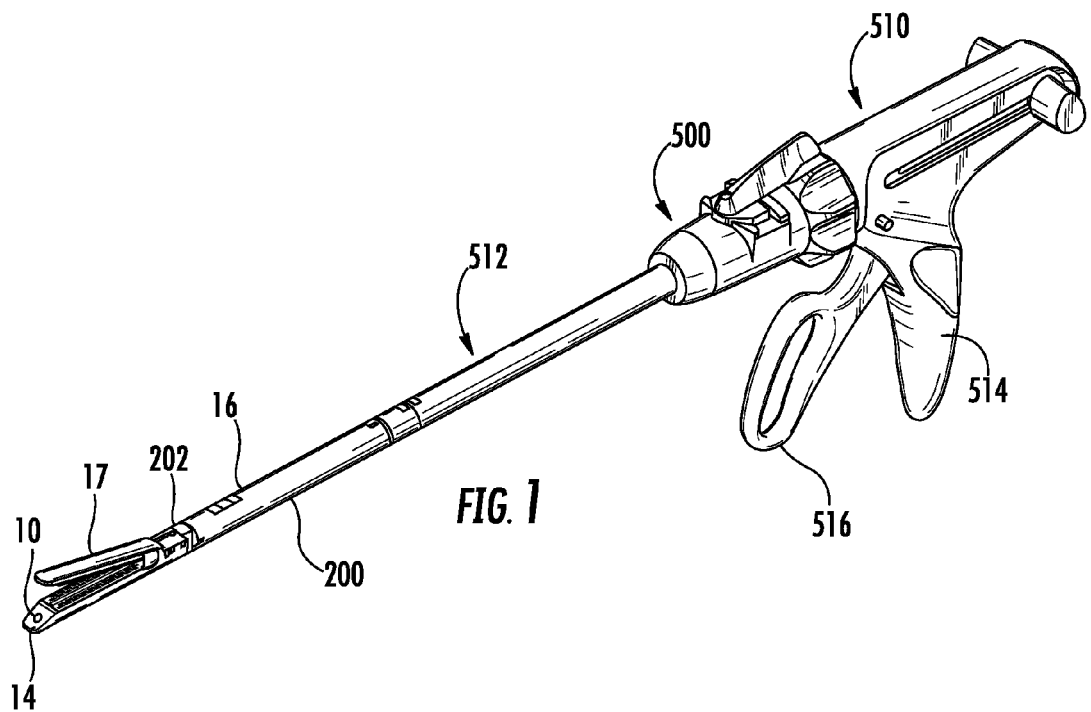
FIG. 1 is a side perspective view of a surgical instrument including a body portion and a disposable loading unit ("DLU") including a tool assembly.

Embodiments of the presently disclosed surgical instrument will now be described in detail with reference to the appended figures, in which like reference numerals designate identical or corresponding elements in each of the several views. In the following description, well known functions or constructions are not described in detail to avoid obscuring the present disclosure in unnecessary detail. As shown in the drawings and as described throughout the following description, and as is traditional when referring to relative positioning on an object, the term proximal refers to the end of the device that is closer to the user and the term "distal" refers to the end of the apparatus that is further from the user.

Figure 1A:
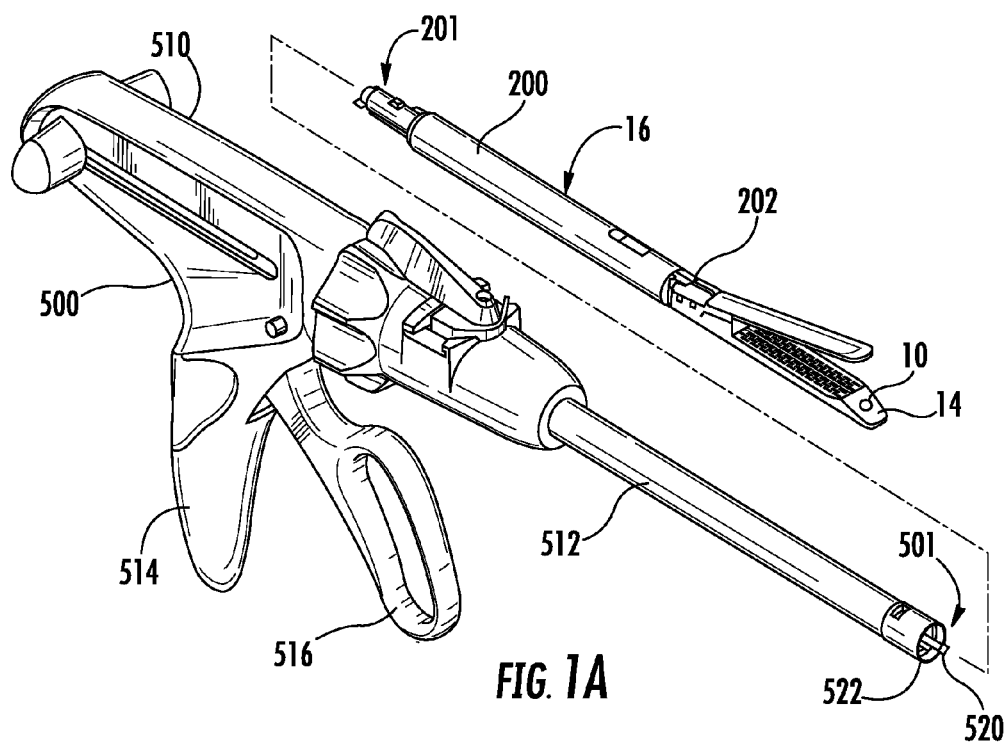
FIG. 1A is a side perspective view of the surgical instrument of FIG. 1 with the DLU separated from the body portion.

A surgical instrument including a DLU including a cartridge having an indicator assembly to provide notification of the condition of the cartridge, i.e., whether the cartridge has been spent, will be described herein. As shown in FIGS. 1 and 1A, a surgical instrument 500 includes a handle portion 510, a body portion 512, and a disposable loading unit ("DLU") 16. The handle portion 510 includes a stationary handle 514 and a movable handle or trigger 516. The movable handle 516 is movable in relation to the stationary handle 514 to actuate the surgical instrument 500. As the movable handle 516 and the stationary handle 514 are moved closer to one another, a control rod 520 is distally advanced from a distal end 501 of the body portion 512. The handle portion 510 and the body portion 512 may be constructed in the manner disclosed in U.S. Pat. No. 6,330,965, which is hereby incorporated by reference in its entirety.

The DLU 16 includes a tool assembly 17, a proximal body portion 200, and a mounting assembly 202. As shown in FIG. 1A, the body portion 200 has a proximal end 201 adapted to releasably engage distal end 501 of the surgical instrument 500. Although as shown in FIG. 1A, the DLU 16 is separable from the body portion 512 of the surgical instrument, in other embodiments, the cartridge itself may be removed from a tool assembly and replaced with a new cartridge. The proximal end 201 of the body portion 200 is linearly inserted into an open end 522 of the body portion 512 of the surgical instrument 500. Actuation of the DLU 16 is facilitated by translation of control rod 520, which engages a proximal end of drive assembly 212 (FIG. 2), thereby causing the drive assembly 212 to translate correspondingly.

The tool assembly 17 may pivot with respect to the longitudinal axis of the body portion 200. Mounting assembly 202 is pivotably secured to a distal end of the body portion 200, and is fixedly secured to a proximal end of tool assembly 17. Pivotal movement of the mounting assembly 202 about an axis perpendicular to a longitudinal axis of body portion 200 causes articulation of tool assembly 17 between a non-articulated position in which the longitudinal axis of tool assembly 17 is aligned with the longitudinal axis of body portion 200 and an articulated position in which the longitudinal axis of tool assembly 17 is disposed at an angle to the longitudinal axis of body portion 200.

An indicator assembly 5 (FIGS. 3A and 3B) minimizes the potential of inadvertent reloading of the DLU 16 after cartridge 54 (FIG. 2) has been spent. As will be explained in greater detail below, at a distal end 14 of the DLU 16, an indicator pin 10 is transitionable between a first position (FIG. 3A) and a second position (FIG. 3B) to indicate whether the cartridge 54 has already been spent. Other embodiments of the indicator assembly 5 are in accordance with the present disclosure. For example, although shown and described as including a single indicator pin 10, a greater number of such pins may be employed. Moreover, although shown and described as extending from the distal end of the cartridge 54, the indicator pin 10 may extend from other surfaces of the cartridge 54 or alternatively from anvil 20. The length and extension of the indicator pin 10 is configured and adapted to maximize the viewability of the indicator pin 10 from multiple orientations.

Figure 2:
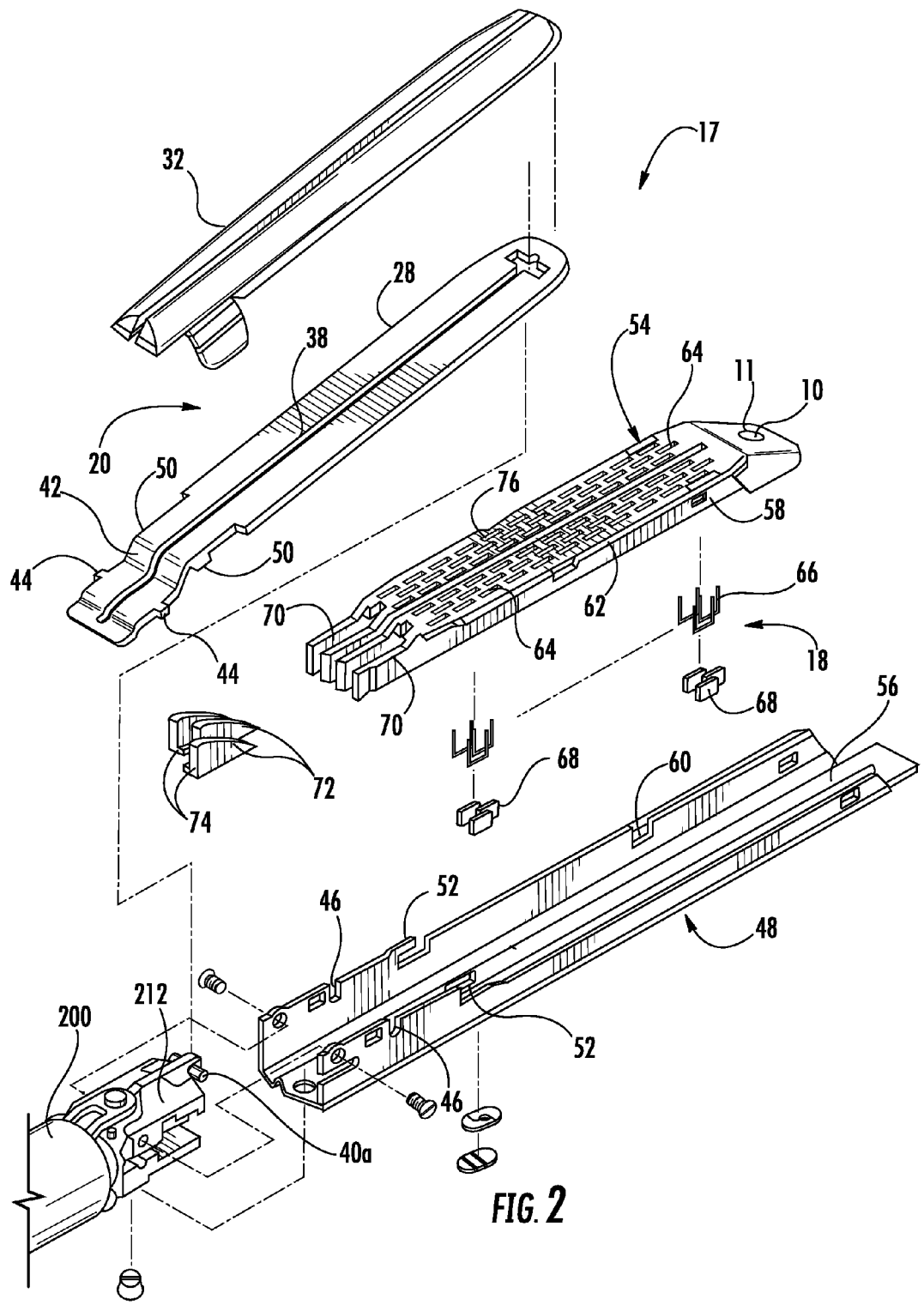
FIG. 2 is a side perspective view of the distal end of DLU of FIG. 1 with parts separated.
Figure 3A:
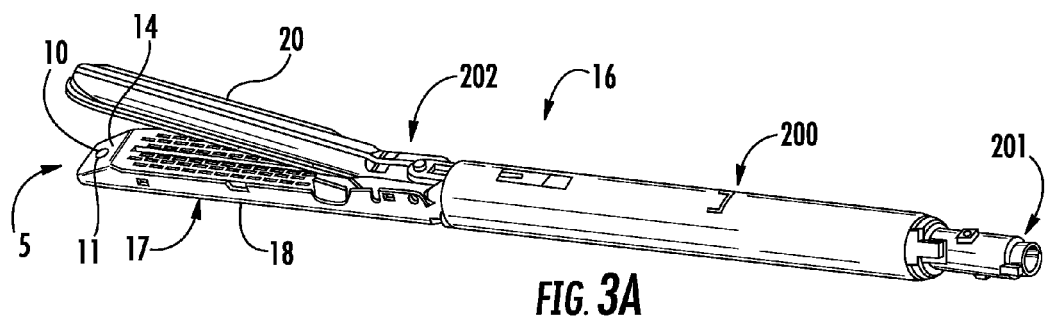
FIG. 3A is a side perspective view of the DLU of FIG. 1 shown in a first position.
Figure 3B:
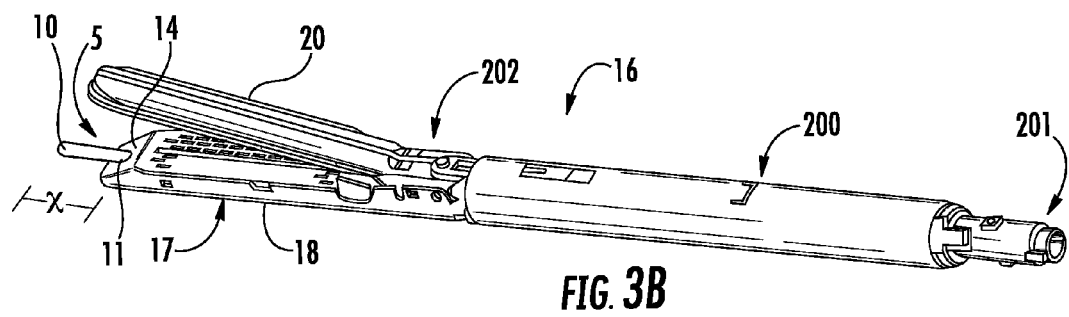
FIG. 3B is the DLU of FIG. 3A shown in a second position.

Referring to FIG. 2, the tool assembly 17 includes a cartridge assembly 18 and an anvil assembly 20. Anvil assembly 20 includes an anvil portion 28 having a plurality of staple deforming concavities 30 (FIG. 4) and a cover plate 32 secured to a top surface of anvil portion 28. The cover plate 32 and the anvil portion 28 define a cavity 34 (FIG. 4) therebetween which is dimensioned to receive a distal end of drive assembly 212 to inhibit pinching of tissue during actuation of DLU 16. A longitudinal slot 38 extends through anvil portion 28 to facilitate passage of a retention flange 40 of drive assembly 212. A camming surface 42 formed on anvil portion 28 is positioned to engage a pair of cam members 40a supported on retention flange 40 of drive assembly 212 to cause approximation of the anvil assembly 20 and the cartridge assembly 18. A pair of stabilizing members 50 engage a respective shoulder 52 formed on carrier 48 to inhibit the anvil portion 28 from sliding axially in relation to staple cartridge 54 as camming surface 42 is pivoted about pivot members 44.

The cartridge assembly 18 includes carrier 48 defining an elongated support channel 56, which is dimensioned and configured to receive staple cartridge 54. Corresponding tabs 58 and slots 60 formed along staple cartridge 54 and elongated support channel 56, respectively, function to retain staple cartridge 54 at a fixed location within support channel 56. A pair of support struts 62 formed on staple cartridge 54 are positioned to rest on side walls of carrier 48 to further stabilize staple cartridge 54 within support channel 56. Carrier 48 has slots 46 for receiving pivot members 44 of anvil portion 28 and allowing anvil portion 28 to move between spaced and approximated positions.

Figure 4:
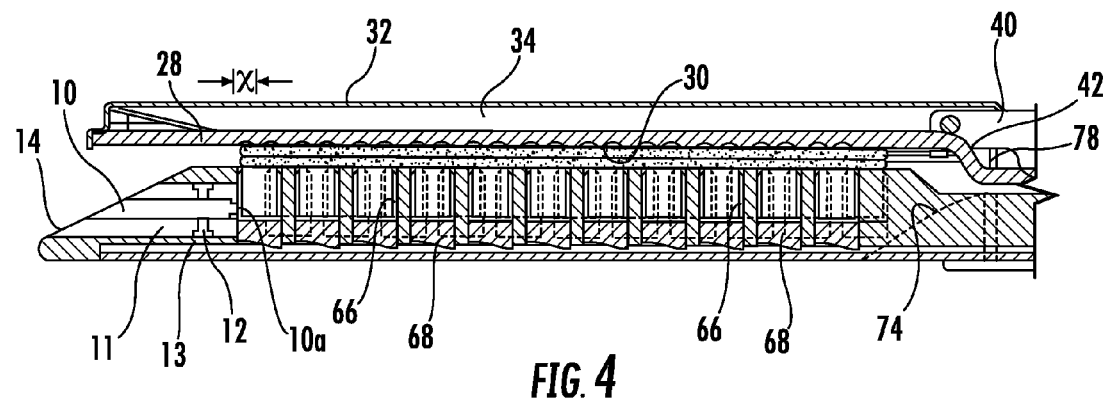
FIG. 4 is a side cross-sectional view of the tool assembly of FIG. 1.

Staple cartridge 54 includes retention slots 64 (FIG. 2) for receiving a plurality of staples or fasteners 66 and pushers 68. A plurality of laterally spaced apart longitudinal slots 70 extend through staple cartridge 54 to accommodate upstanding cam wedges 72 of an actuation sled 74 (FIG. 2), which is operatively coupled to the drive assembly 212. A central longitudinal slot 76 extends along substantially the length of staple cartridge 54 to facilitate passage of a knife blade 78 (FIG. 4). During operation, drive assembly 212 abuts actuation sled 74 and pushes actuation sled 74 through longitudinal slots 70 of staple cartridge 54 to advance cam wedges 72 into sequential contact with pushers 68. Pushers 68 translate vertically along cam wedges 72 within fastener retention slots 64 and urge fasteners 66 from retention slots 64 into the staple deforming concavities 30 of anvil assembly 20.

Figure 5:
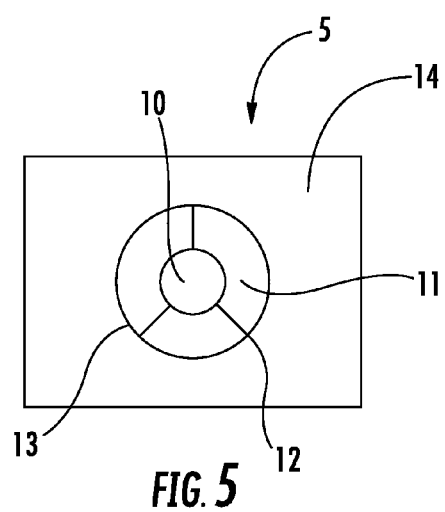
FIG. 5 is a side view of the distal end of the tool assembly of FIG. 1.

As shown in FIGS. 4 and 5, the indicator pin 10 is positioned within a channel 11 that extends through distal end 14 of the staple cartridge 54. The channel 11 may narrow toward the distal end 14 of the staple cartridge 54 such that distal translation of the indicator pin 10 through the channel 11 will frictionally secure the indicator pin 10 within the channel, thereby inhibiting proximal translation of the indicator pin 10 back through the channel 11 once the indicator pin 10 has been fully translated through the channel 11. The indicator pin 10 may be releasably locked within a ring 13. One or more frangible fingers 12 may operatively couple the indicator pin 10 to the ring 13. As the actuation sled 74 translates through the staple cartridge 54, the force of the actuation sled 74 abutting the proximal end 10a of the indicator pin 10 will break the frangible fingers 12, thereby permitting distal translation of the indicator pin 11 through the channel 11.

During use of the surgical instrument 500, a surgeon will place tissue (not shown) that is to be stapled between the anvil assembly 20 and the cartridge assembly 18 to join tissue therebetween. As the surgical instrument 500 is fired, the indicator assembly 5 transitions to a position indicating that surgical instrument 500 has been fired and the cartridge 54 has been spent. As discussed above, the indicator pin 10 extends from a surface and is readily viewable from multiple orientations. The surgical instrument 500 is removed from the surgical site, and if necessary, the DLU 16 is replaced with a DLU 16 including a cartridge 54 that is in a condition to be fired.

It will be understood that various modifications may be made to the embodiments disclosed herein. Although the indicator assembly is shown being used with a surgical stapling device, the indicator assembly may be incorporated into any surgical device having a cartridge. The indicator assembly will provide notification that the cartridge has been spent, thereby alerting a user to provide a fresh cartridge. Therefore, the above description should not be construed as limiting, but merely as exemplifications of various embodiments. Those skilled in the art will envision other modifications within the scope and spirit of the claims appended hereto.

What is claimed is:

1. A surgical instrument comprising:
   a body portion;
   a loading unit operatively coupled to the body portion, the loading unit including a cartridge having a distal portion, the cartridge housing a plurality of fasteners;
   a longitudinally extending aperture defined within the distal portion;
   a drive assembly configured to translate through the cartridge to eject the plurality of fasteners from the cartridge; and
   an indicator assembly transitionable from a first position to a second position after ejection of the plurality of fasteners, the indicator assembly including:
      an indicator pin translatable through the longitudinally extending aperture, the indicator pin being substantially flush with a surface of the cartridge when the indicator assembly is in the first position, and extending past the surface of the cartridge when the indicator assembly is in the second position,
      a ring positioned within the longitudinally extending aperture and disposed around the indicator pin, and
      at least one frangible finger joining the indicator pin and the ring, the at least one frangible finger inhibiting transitioning of the indicator pin from the first to the second position prior to actuation of the surgical instrument, the at least one frangible finger breaking in response to actuation of the surgical instrument.

2. The surgical instrument of claim 1, wherein the indicator assembly is frictionally inhibited from transitioning from the second position to the first position.

3. The surgical instrument of claim 2, wherein the indicator pin is frictionally inhibited from transitioning from the second position to the first position.

4. The surgical instrument of claim 1, wherein distal translation of the drive assembly causes the indicator assembly to transition to the second position.

5. The surgical instrument of claim 4, wherein actuation of the surgical instrument translates the indicator pin from the first position to the second position.

6. The surgical instrument of claim 5, wherein translation of the indicator pin from the first position to the second position breaks the at least one frangible finger.

7. The surgical instrument of claim 1, wherein the longitudinally extending aperture narrows from a proximal end to a distal end of the longitudinally extending aperture.

8. The surgical instrument of claim 7, wherein distal translation of the indicator pin through the longitudinally extending aperture frictionally secures the indicator pin within the longitudinally extending aperture, thereby inhibiting proximal translation of the indicator pin back through the longitudinally extending aperture.

9. The surgical instrument of claim 1, wherein the loading unit is separable from the body portion.

10. A method of performing a surgical procedure comprising:
   providing a surgical instrument including:
      a body portion;
      a loading unit operatively coupled to the body portion, the loading unit including a cartridge with a distal portion, the cartridge housing a plurality of fasteners, and an anvil movable relative to the cartridge;
      a longitudinally extending aperture defined within the distal portion;
      a drive assembly translatable through the cartridge to eject the plurality of fasteners from the cartridge; and
      an indicator assembly transitionable from a first position to a second position after ejection of the plurality of fasteners, the indicator assembly including:
         an indicator pin translatable through the longitudinally extending aperture, the indicator pin being substantially flush with a surface of the cartridge when the indicator assembly is in the first position, and extending past the surface of the cartridge when the indicator assembly is in the second position,
         a ring positioned within the longitudinally extending aperture and disposed around the indicator pin, and
         at least one frangible finger joining the indicator pin and the ring, the at least one frangible finger inhibiting transitioning of the indicator pin from the first to the second position prior to actuation of the surgical instrument, the at least one frangible finger breaking in response to actuation of the surgical instrument;
   placing tissue between the cartridge and the anvil;
   actuating the surgical instrument to fasten the tissue placed between the cartridge and the anvil;
   observing the indicator assembly in the second position; and
   separating the loading unit from the surgical instrument.

* * * * *